US008475529B2

(12) United States Patent
Clarke

(10) Patent No.: US 8,475,529 B2
(45) Date of Patent: Jul. 2, 2013

(54) ACCOMMODATING INTRAOCULAR LENS

(76) Inventor: Gerald P. Clarke, Menasha, WI (US)

( * ) Notice: Subject to any disclaimer, the term of this patent is extended or adjusted under 35 U.S.C. 154(b) by 81 days.

(21) Appl. No.: 13/134,790

(22) Filed: Jun. 17, 2011

(65) Prior Publication Data

US 2012/0035724 A1 Feb. 9, 2012

Related U.S. Application Data

(62) Division of application No. 11/185,279, filed on Jul. 19, 2005, now Pat. No. 8,038,711.

(51) Int. Cl.
*A61F 2/16* (2006.01)

(52) U.S. Cl.
USPC ........................................................ 623/6.43

(58) Field of Classification Search
USPC ....... 623/6.11, 6.13, 6.37–6.41, 23.64–23.65; 606/191; 600/37; 128/898
See application file for complete search history.

(56) References Cited

U.S. PATENT DOCUMENTS

| | | | |
|---|---|---|---|
| 4,254,509 A | 3/1981 | Tennant |
| 4,298,996 A | 11/1981 | Barnet |
| 4,373,218 A | 2/1983 | Schachar |
| 4,409,691 A | 10/1983 | Levy |
| 4,424,597 A | 1/1984 | Schlegel |
| 4,573,998 A | 3/1986 | Mazzocco |
| 4,664,666 A | 5/1987 | Barrett |
| 4,673,406 A | 6/1987 | Schlegel |
| 4,685,921 A | 8/1987 | Peyman |
| 4,738,680 A | 4/1988 | Herman |
| 4,753,655 A | 6/1988 | Hecht |
| 4,778,463 A | 10/1988 | Hetland |
| 4,813,955 A | 3/1989 | Achatz et al. |
| 4,840,627 A | 6/1989 | Blumenthal |
| 4,842,601 A | 6/1989 | Smith |
| 4,888,012 A | 12/1989 | Horn et al. |

(Continued)

FOREIGN PATENT DOCUMENTS

| | | |
|---|---|---|
| EP | 0812166 | 12/1997 |
| WO | 2004010904 | 2/2004 |
| WO | 2005048882 | 6/2005 |
| WO | 2007106796 | 9/2007 |

OTHER PUBLICATIONS

Okihiro Nishi et al., Capsular bag refilling using a new accommodating intraocular lens, J Cataract Refract Surg, Feb. 2008, 8 pages, vol. 34, Elsevier Inc.

(Continued)

*Primary Examiner* — William H Matthews
(74) *Attorney, Agent, or Firm* — Thomas D. Wilhelm; Wilhelm Law, S.C.

(57) ABSTRACT

An accommodating intraocular lens, for use in an eye, is made from flexible, optionally elastic, bio-compatible lens body material surrounding a closed and sealed lens cavity. One or more compressible struts is in the cavity. The cavity is filled with bio-compatible optical liquid. The optical liquid has a refractive index sufficiently high to, in cooperation with the ciliary muscle and the compressible strut, focus light, incident on the eye, on the retina, thus to provide accommodation. The curvature of the surface of the lens is deformable, by the forces expressed by the ciliary body and the strut, thus to change the radius of curvature of the anterior body member and/or the posterior body member, thus providing focusing, including from relatively farther distance in the relaxed state to relatively nearer distance in the accommodative state.

18 Claims, 7 Drawing Sheets

U.S. PATENT DOCUMENTS

| | | | |
|---|---|---|---|
| 4,932,966 A | 6/1990 | Christie et al. |
| 4,963,148 A | 10/1990 | Sulc et al. |
| 4,994,082 A | 2/1991 | Richards et al. |
| 4,994,083 A | 2/1991 | Sulc et al. |
| 5,035,710 A | 7/1991 | Nakada et al. |
| 5,047,051 A | 9/1991 | Cumming |
| 5,476,514 A | 12/1995 | Cumming |
| 5,674,282 A | 10/1997 | Cumming |
| 6,096,078 A | 8/2000 | McDonald |
| 6,197,059 B1 | 3/2001 | Cumming |
| 6,299,641 B1 | 10/2001 | Woods |
| 6,406,494 B1 | 6/2002 | Laguette et al. |
| 6,478,821 B1 | 11/2002 | Laguette et al. |
| 6,494,911 B2 | 12/2002 | Cumming |
| 6,503,276 B2 | 1/2003 | Lang et al. |
| 6,558,420 B2 | 5/2003 | Green |
| 6,599,317 B1 | 7/2003 | Weinschenk et al. |
| 6,638,305 B2 | 10/2003 | Laguette |
| 6,767,363 B1 | 7/2004 | Bandhauer et al. |
| 6,855,164 B2 | 2/2005 | Glazier |
| 7,025,783 B2 | 4/2006 | Brady et al. |
| 7,122,053 B2 | 10/2006 | Esch |
| 7,125,422 B2 | 10/2006 | Woods et al. |
| 7,217,288 B2 | 5/2007 | Esch et al. |
| 7,220,279 B2 | 5/2007 | Nun |
| 7,261,737 B2 | 8/2007 | Esch et al. |
| 2002/0193876 A1 | 12/2002 | Lang et al. |
| 2004/0111153 A1 | 6/2004 | Woods et al. |
| 2005/0119739 A1 | 6/2005 | Glazier |
| 2005/0137703 A1 | 6/2005 | Chen |
| 2005/0143812 A1 | 6/2005 | Paul et al. |
| 2005/0149183 A1 | 7/2005 | Shadduck |
| 2005/0246018 A1 | 11/2005 | Grubbs et al. |
| 2005/0251253 A1* | 11/2005 | Gross ............................ 623/6.13 |
| 2006/0271186 A1 | 11/2006 | Nishi et al. |
| 2007/0213817 A1 | 9/2007 | Esch et al. |
| 2008/0033547 A1 | 2/2008 | Chang et al. |
| 2009/0043384 A1 | 2/2009 | Niwa et al. |
| 2012/0179248 A1* | 7/2012 | Azar ............................ 623/6.37 |

OTHER PUBLICATIONS

De-Ying Zhang et al., Fluidic adaptive lens with high focal length tunability, Applied Physics Letters, May 13, 2003, 2 pages, vol. 82, No. 19.

Wen Qiao et al., Fluidic Intraocular Lens With a Large Accommodation Range, IEEE Photonics Technology Letters, Mar. 1, 2009, 3 pages, vol. 21, No. 5.

Achim Langenbucher et al., Pseudophakic accommodation with translation lenses—dual optic vs. mono optic, Apr. 2, 2004, 8 pages, Department of Ophthalmology, University of Er.

* cited by examiner $$\text{Sys} := \left(\begin{array}{l} 1 - Pi1 \cdot Da - Dc \cdot Pc2 + Dc \cdot Pc2 \cdot Pi1 \cdot Da - Dc \cdot Pi1 + Pi2 \cdot Di \cdot Dc \cdot Pi1 \cdot Da - Pi2 \cdot Di \cdot Dc \cdot Pc2 + \\ \quad Di - Di \cdot Pi1 \cdot Da - Di \cdot Dc \cdot Pc2 + Di \cdot Dc \cdot Pc2 \cdot Pi1 \cdot Da - \\[4pt] Pi2 \cdot Di \cdot Dc \cdot Pc2 \cdot Pi1 \cdot Da - Pi2 \cdot Di \cdot Dc \cdot Pi1 + Pi2 \cdot Da - Pi2 \cdot Dc \cdot Da \cdot Pc2 + Pi2 \cdot Dc - Pc1 + \\ \quad Di \cdot Dc \cdot Pi1 + Da - Dc \cdot Da \cdot Pc2 + Dc \\[4pt] Pc1 + Pc1 \cdot Pi1 \cdot Da + Pc1 \cdot Dc \cdot Pc2 - Pc1 \cdot Dc \cdot Pc2 \cdot Pi1 \cdot Da + Pc1 \cdot Dc \cdot Pi1 - Pc2 + Pc2 \cdot Pi1 \cdot Da - Pi1 - \\ \quad - Di \cdot Pc1 + Di \cdot Pc1 \cdot Pi1 \cdot Da + \\[4pt] Pi2 \cdot Di \cdot Pc1 + Pi2 \cdot Di \cdot Pc1 \cdot Pi1 \cdot Da + Pi2 \cdot Di \cdot Pc1 \cdot Dc \cdot Pc2 \\ \quad Di \cdot Pc1 \cdot Dc \cdot Pc2 - Di \cdot Pc1 \cdot Dc \cdot Pc2 \cdot Pi1 \cdot Da + Di \cdot Pc1 \cdot Dc \cdot Pi1 \\[4pt] - Pi2 \cdot Di \cdot Pc1 \cdot Dc \cdot Pc2 \cdot Pi1 \cdot Da + Pi2 \cdot Di \cdot Pc1 \cdot Dc \cdot Pi1 - Pi2 \cdot Di \cdot Pc2 + Pi2 \cdot Di \cdot Pc2 \cdot Pi1 \cdot Da - Pi2 \cdot Di \cdot Pi1 \cdot \\ \quad - Pc1 \cdot Da + Pc1 \cdot Dc \cdot Da \cdot Pc2 - Pc1 \cdot Dc - Da \cdot Pc2 + 1 \\[4pt] Pi2 \cdot Pc1 \cdot Da + Pi2 \cdot Pc1 \cdot Dc \cdot Da - Pi2 \cdot Pc1 \cdot Dc - Pi2 \cdot Da \cdot Pc2 + Pi2 \end{array}\right)$$

Solving    Pi1 := 1
            Given

Second Focal Point: is Vit (t3)

$$Vit = -Ng \cdot \frac{-Pc1 + Pc1 \cdot Pi1 \cdot Da + Pc1 \cdot Dc \cdot Pc2 - Pc1 \cdot Dc \cdot Pc2 \cdot Pi1 \cdot Da + Pc1 \cdot Dc \cdot Pi1 - Pc2 + Pc2 \cdot Pi1 \cdot Da - Di \cdot Pc1 + Di \cdot Pc1 \cdot}{Pi1 \cdot Da + Di \cdot Pc1 \cdot Dc \cdot Pc2 - Di \cdot Pc1 \cdot Dc \cdot Pc2 \cdot Pi1 \cdot Da + Di \cdot Pc1}$$

$$\frac{Pi1 - Pi2 \cdot Di \cdot Pc1 + Pi2 \cdot Di \cdot Pc1 \cdot Pi1 \cdot Da + Pi2 \cdot Di \cdot Pc1 \cdot Dc \cdot Pc2}{-Dc \cdot Pi1 - Di \cdot Pc2 + Di \cdot Pc2 \cdot Pi1 \cdot Da - Di \cdot Pi1 - Pc1 \cdot Da +}$$

$$\frac{-Pi2 \cdot Di \cdot Pc1 \cdot Dc \cdot Pc2 \cdot Pi1 \cdot Da + Pi2 \cdot Di \cdot Pc1 \cdot Dc \cdot Pi1 -}{Pc1 \cdot Dc \cdot Da \cdot Pc2 - Pc1 \cdot Dc - Da \cdot Pc2 + 1}$$

$$Pi2 \cdot Di \cdot Pc2 + Pi2 \cdot Di \cdot Pc2 \cdot Pi1 \cdot Da - Pi2 \cdot Di \cdot Pi1 - Pi2 \cdot Pc1 \cdot Dc \cdot Da + Pi2 \cdot Pc1 \cdot Dc \cdot Da \cdot Pc2 - Pi2 \cdot Pc$$

ACCOMMODATING INTRAOCULAR LENS

CROSS REFERENCE TO RELATED APPLICATIONS

This application is a Divisional of application Ser. No. 11/185,279, filed Jul. 19, 2005, which is now U.S. Pat. No. 8,038,711, granted Oct. 18, 2011.

BACKGROUND

This invention relates generally to manufactured intraocular lenses and more particularly to novel accommodating intraocular lenses for implantation in the eye specifically within the capsular bag, or in the ciliary sulcus, of the eye from which the natural lens matrix has been removed. The invention also relates to a novel method of utilizing the intraocular lenses in the eye to provide the patient with lens accommodation capability, responsive to normal accommodative ciliary muscle action.

The human eye has an anterior chamber between the cornea and the iris, and a posterior chamber behind the iris, which contains a natural crystalline lens. A vitreous chamber behind the lens contains vitreous humor. A retina is located to the rear of the vitreous chamber. The crystalline lens of a normal human eye is defined by a crystalline lens matrix, which is enclosed in a lens capsule. The lens capsule is attached about its periphery to the ciliary muscle of the eye by zonules. The lens capsule has elastic, optically clear, anterior and posterior membrane-like walls commonly referred by ophthalmologists as anterior and posterior capsules, respectively. Between the iris and ciliary muscle is an annular crevice-like space called the ciliary sulcus.

The human eye possesses natural accommodation capability. Accommodation refers to an optical function in which the lens can focus naturally, from a far distance, to a relatively near distance e.g. within a few centimeters of the eye. Natural accommodation involves relaxation and constriction of the ciliary muscle, as instructed by the brain, to provide the eye with near and distant vision. This ciliary muscle action is automatic, as instructed by the brain, and shapes the natural crystalline lens to the appropriate optical configuration for focusing, on the retina, the light rays entering the eye from the scene being viewed. It is well known that there is a relentless loss of this near focusing ability in middle age. Such condition can be treated with bi-focal or tri-focal glasses or contact lenses.

The human eye is also subject to a variety of other physiological disorders, which can degrade, or totally destroy, the ability of the eye to function properly. One of the more common of these disorders involves progressive clouding of the natural crystalline lens matrix resulting in the formation of what is commonly referred to as a cataract. It is now common practice to treat a cataract by surgically removing the cataractous human crystalline lens and, in a second step of the same surgical procedure, implanting an artificial intraocular lens in the eye to replace the natural lens.

Thus, if the natural lens becomes cloudy, as with a cataract condition, the natural lens is removed by an extraction procedure which leaves intact, within the eye, the posterior portion of the natural lens capsule, and at least a remnant of the anterior portion of the natural lens capsule. The removed natural lens is replaced with a manufactured intraocular lens. If the replacement lens is a mono-focal lens, the cloudiness may have been effectively treated, but the inability to adjust focal length will not have been treated, whereby glasses or contact lenses are still required for proper vision.

Monofocal lenses focus at one set focal length in front of the eye, for example either at far distance such as greater than 6 meters, or at a lesser distance nearer the eye. The human eye with its own natural lens can change shape, thereby to focus naturally at all such distances, but gradually loses this ability, to change shape, as the natural lens hardens with age. The ability of the natural lens, to change shape as so urged by the contraction of the ciliary muscle, thus to change focal length of the eye, whereby the eye can focus at any of a range of distances, is completely lost after cataract surgery when the manufactured replacement lens is a monofocal lens.

Newer designs of conventional manufactured intraocular lenses offer differing solutions to this problem of loss of accommodation. One such design is a lens which has a single posteriorly placed optic and hinged haptics, which enables the lens to translate forward with the pressure rise in the vitreous chamber, which pressure rise accompanies accommodation as signaled from the brain. The limitation of this design is that the maximum accommodation enabled by lens translation is typically only about 1.5 diopters for a 1 mm anterior translation of the lens. While a 1 mm translation is typical, modest differences in translation capability attend respective different eyes. Thus, actual diopter achievements depend both on the power of the intraocular lens, and the axial length of the eye.

Another relatively newer conventional manufactured intraocular lens design uses two lenses, which are hinged, or otherwise connected, together and implanted inside the natural lens capsular bag. The anterior manufactured lens has e.g. high plus power, while the posterior manufactured lens has a negative power. When the two lenses separate under accommodative tension, the anterior lens moves forward and the posterior lens moves backward, achieving a relatively higher calculated accommodation, which is less dependent on intraocular lens powers and/or axial lengths of the eye.

Yet another conventional intraocular lens design provides multiple lens elements or components in side-by-side relationship, in a single lens body, the respective side-by-side lens elements having different, but fixed, refractive powers.

Still another conventional intraocular lens design provides an intraocular lens which consists of a flexible transparent lens envelope filled with a transparent fluid. The envelope is attached to the ciliary muscle by means of a fastening fringe, which is in turn anchored to the lens envelope. The ciliary muscle acts as it does on the natural lens. Thus, when the ciliary muscle contracts, the lens becomes more spherical, and thus achieves a greater refractory power. When the ciliary muscle elongates, tension is exerted on the envelope, and flattens the envelope, reducing refracting power, which accommodates far vision.

SUMMARY

The current invention comprehends an accommodating intraocular lens made from flexible, optionally elastic, biocompatible lens body material surrounding a closed and sealed lens cavity which is filled with bio-compatible optical liquid, such as a gel, or an oil-based optical composition, which has a refractive index sufficiently greater than the refractive index of the vitreous humor in the eye, that changes in shape of the optical liquid satisfy the optical requirements for achieving accurate and accommodative focus on the retina, while being sufficiently deformable to change the curvature of the anterior and/or the posterior intraocular lens surfaces to allow accommodation—near focus—to occur as in the natural state for the youthful eye, by operation of the optical liquid in the cavity in accord with the change in curvature of the anterior and/or posterior surfaces of the optical liquid.

Namely, change in radius of curvature in the lens body automatically changes the corresponding radius of curvature of the effective surface of the contained optical liquid which is at the respective location adjacent the lens body in the lens cavity. The refractive index of the optical liquid in the lens cavity is greater than the refractive index of the vitreous humor, which is approximately equal to the refractive index of water, which is namely about 1.33. A suitable refractive index for the optical liquid in the cavity is about 1.40. An exemplary suitable composition for the optical composition, having such suitable refractive index, is optical grade silicone oil, alternatively hyaluronic acid, or its ester, with suitable additives for providing the desired physical properties such as viscosity.

A first family of embodiments of lenses of the invention comprehends an accommodating intraocular lens, comprising a bio-compatible optical lens body having an anterior body member and a posterior body member, joined to each other. The optical lens body defines a vision axis, and an optical lens body outer perimeter which extends about the vision axis. At least one of the anterior body member and the posterior body member has a convex radius of curvature, which has an origin on the vision axis. The lens further comprises a closed and sealed cavity in the lens body, extending generally outwardly away from the vision axis. The lens still further comprises a bio-compatible liquid filling the cavity, the liquid having a refractive index greater than the refractive index of water, and connecting structure attached to the optical lens body at or adjacent the outer perimeter of the optical lens body. The connecting structure is effective to interface with a ciliary muscle, and to transmit forces, exerted by the ciliary muscle, related to contraction or relaxation of the ciliary muscle, on the connecting structure, to the optical lens body at or adjacent the outer perimeter of the lens body, thereby to cause the force so received by the lens body to effect change in radius of curvature of at least one of the anterior body member and the posterior body member.

In some embodiments, the connecting structure comprises a flange which extends outwardly from the outer perimeter of the lens body, away from the vision axis, the flange having sufficient rigidity to transmit forces, exerted by the ciliary muscle, which urge reduction in length of the outer perimeter of the optical lens body, to the outer perimeter of the optical lens body.

In some embodiments, the anterior body member has convex outer and inner surfaces, and the posterior body member has a planar or concave or otherwise recessed inner surface.

In some embodiments, the posterior body member is more rigid than the anterior body member, whereby imposition of an inwardly-directed force against an outer edge of the flange results in deflection of the anterior body member in preference to deflection of the posterior body member.

In some embodiments, the anterior body member has inner and outer surfaces, the outer surface defines a convex configuration, the inner surface has a corresponding convex configuration which follows the configuration of the outer surface, and the inner and outer surfaces optionally are defined by compound radii of curvature when tracked through the vision axis.

In some embodiments, each of the inner and outer surfaces is defined by a single center of rotation located on the vision axis.

In some embodiments, at least one of the inner and outer surfaces is defined by multiple centers of rotation.

In some embodiments both the anterior body member and the posterior body member have convex inner surfaces.

In some embodiments, the compositions of the anterior body member and the posterior body member are selected from the group consisting of optical grade silicone, polymerized collagen, optical elastic acrylic polymer, collamer, and combinations of collamer and hydroxyethyl methacrylate.

In some embodiments, the composition of the bio-compatible filling liquid is selected from the group consisting of silicone oil, hyaluronic acid, and salts of hyaluronic acid.

In some embodiments, the filing liquid has a refractive index of at least 1.35, and is optionally birefringent.

In some embodiments, the filing liquid has a refractive index of at least 1.40.

In a second family of embodiments, the invention comprehends a method of providing focal length adjustment in an eye of a patient in need of a replacement intraocular lens. The method comprises installing in the eye an accommodating intraocular lens, which comprises a bio-compatible optical lens body having an anterior body member and a posterior body member, joined to each other, the optical lens body defining a vision axis, and an optical lens body outer perimeter which extends about the vision axis, at least one of the anterior body member and the posterior body member having a radius of curvature having an origin on the vision axis, a closed and sealed cavity in the lens body, extending generally outwardly away from the vision axis, and a bio-compatible liquid, filling the cavity, the liquid having a refractive index greater than the refractive index of water. The method further comprises interfacing connecting structure of the intraocular lens, such as a flange, to a ciliary muscle of the patient such that the connecting structure is effective to receive change in forces accompanying change in muscle contraction or relaxation, and to transmit such change in forces to the optical lens body at or adjacent the outer perimeter of the optical lens body, thereby to cause the force changes so received by the lens body to effect change in radius of curvature of at least one of the anterior body member and the posterior body member.

In some embodiments, the eye of the patient has a natural lens capsule, having a circumferential outer edge, the connecting structure of the lens comprises a flange extending from the outer perimeter of the lens body, the flange has sufficient rigidity to transmit, to the lens body, forces exerted by the ciliary muscle, on the natural lens capsule, which urge reduction in length of the outer perimeter of the optical lens body. The corresponding method comprises installing the intraocular lens such that the outer edge of the flange is inside the lens capsule, and adjacent the outer edge of the lens capsule, such that the flange is sensitive to activity of the ciliary muscle, and transmits the change forces to the optical lens body, thereby to provide focal length accommodation.

In some embodiments, the posterior body member is rigid relative to the anterior body member, such that changes in the radius of curvature of the anterior body member, by flexure of the anterior body member, causes changes, in focal length of the liquid filling, which are substantially greater than any changes in focal length caused by flexure of the posterior body member.

In some embodiments, the eye of the patient comprises a sulcus, and the method further comprises positioning the outer edge of the flange in the sulcus.

In some embodiments, both the anterior lens body and the posterior lens body define convex inner and outer surfaces, and respond to flexure of the ciliary muscle with similar changes in radius of curvature.

In some embodiments, inner and outer surfaces of the at least one convex body member having substantially the same radii of curvature.

In a third family of embodiments, the invention comprehends an accommodating intraocular lens, comprising a bio-compatible optical lens body having an anterior body member and a posterior body member, joined to each other, the optical lens body defining a vision axis, and an optical lens body outer perimeter which extends about the vision axis, at least one of the anterior body member and the posterior body member having a radius of curvature having an origin on the vision axis; the joinder of the anterior lens body member and the posterior lens body member defining a cavity therebetween, in the lens body, the cavity extending generally outwardly away from the vision axis; one or more compressible struts in the cavity, extending between the anterior lens body member and the posterior lens body member, the one or more struts being displaced from the vision axis, and being configured to flex away from the vision axis when compressed; and a bio-compatible liquid filling in the cavity, the liquid having a refractive index greater than the refractive index of water.

BRIEF DESCRIPTION OF THE DRAWINGS

FIGS. 10-11 show expanded representations of the mathematical matrices discussed in Langenbucher.

Figure 1:
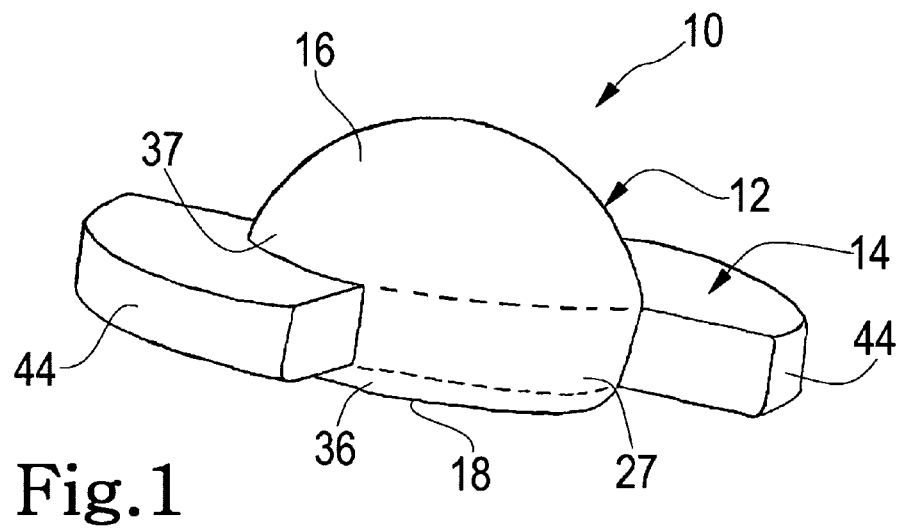
FIG. 1 shows a generally front pictorial view of a first embodiment of a lens of the invention.

The invention is not limited in its application to the details of construction or the arrangement of the components set forth in the following description or illustrated in the drawings. The invention is capable of other embodiments or of being practiced or carried out in other various ways. Also, it is to be understood that the terminology and phraseology employed herein is for purpose of description and illustration and should not be regarded as limiting. Like reference numerals are used to indicate like components.

DESCRIPTION OF THE ILLUSTRATED EMBODIMENTS

A first family of embodiments of accommodating intraocular lenses 10 of the invention is illustrated in FIGS. 1-4. FIG. 5 shows an exemplary such lens implanted in an eye.

Lens 10 includes a lens body 12, and first and second flanges 14. Lens body 12 includes a convex anterior body member 16 and a generally planar posterior body member 18. Anterior body member 16 has an inner surface 20 and an outer surface 22. Posterior body member 18 has an inner surface 24 and an outer surface 26. Anterior body member 16 and posterior body member 18 are joined to each other at an outer perimeter 27 of the lens body.

A vision axis 28 extends through the lens body, generally centered with respect to outer perimeter 27 of the lens body. Vision axis 28 generally passes through the apex of the convex arc which is defined by anterior body member 16, and also passes through the center of the posterior body member. Thus vision axis 28 is generally centered on the lens body, and passes front-to-rear through the lens body, as through the center of the anterior body member and the center of the posterior body member.

Figure 2:
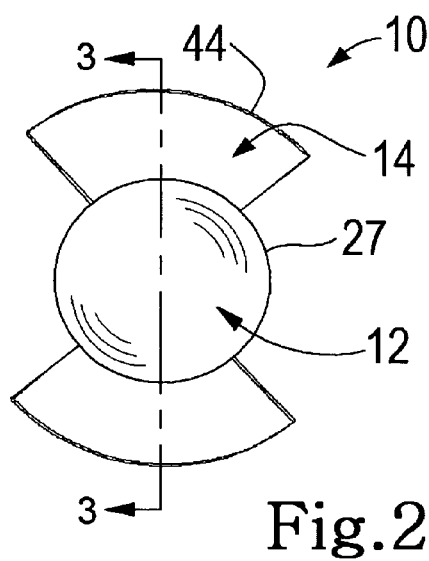
FIG. 2 shows a front view of the lens of FIG. 1.
Figure 4:
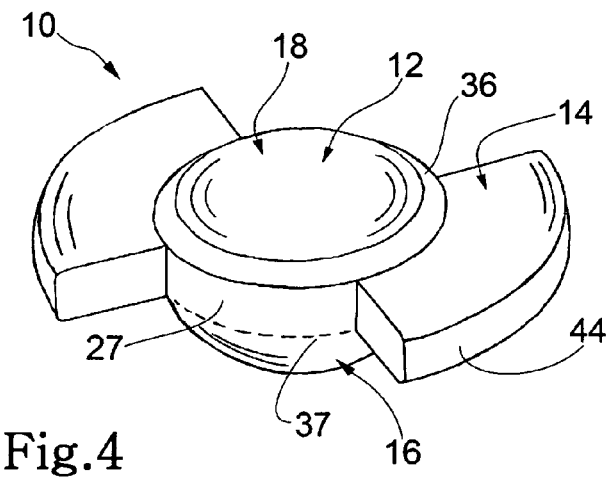
FIG. 4 shows a rear pictorial view of the lens of FIGS. 1-3.
Figure 5:
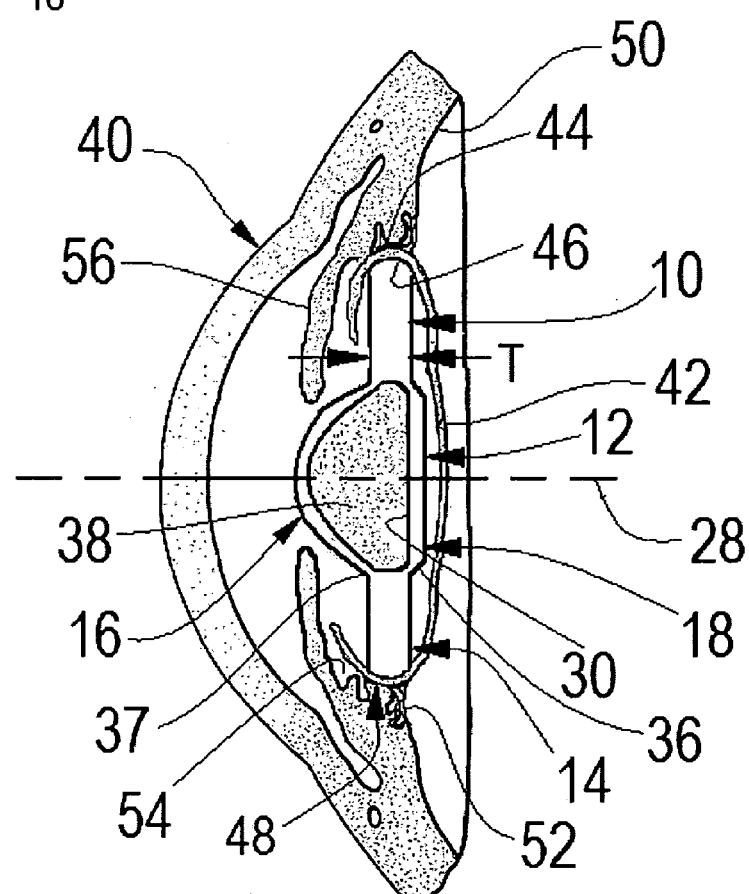
FIG. 5 is a cross-section view illustrating the lens of FIGS. 1-4 implanted in an eye.

As illustrated in FIGS. 1, 2, and 4, flanges 14 are connected to the lens body at outer perimeter 27, at opposing sides of the lens body, and extend from the lens body in opposing directions which are generally perpendicular to the direction of extension of the vision axis or at a small angle to such perpendicular, e.g. no more than 10 degrees.

Between the anterior body member and the posterior body member is a closed and sealed cavity 30 which is generally defined by the inner surfaces 20, 24 of the anterior body member and the posterior body member. In the illustrated embodiment, cavity 30 has a cross-section which is generally constant, or nearly constant, when turned about the vision axis. Given the shapes of the inner surfaces of the anterior and posterior body members, cavity 30 has a cross-section which generally resembles a hemisphere.

Figure 3:
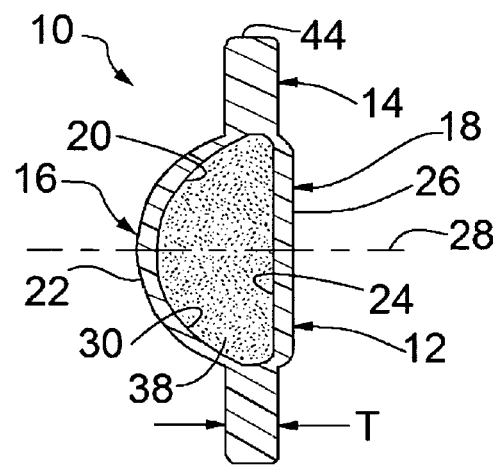
FIG. 3 shows a side cross-section view of the lens of FIGS. 1 and 2, taken at 3-3 of FIG. 2.
Figure 6:
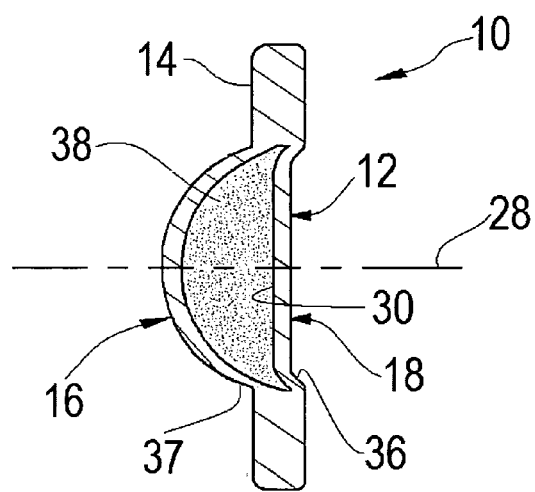
FIG. 6 shows a cross-section view of a second embodiment of lenses of the invention.
Figure 7:
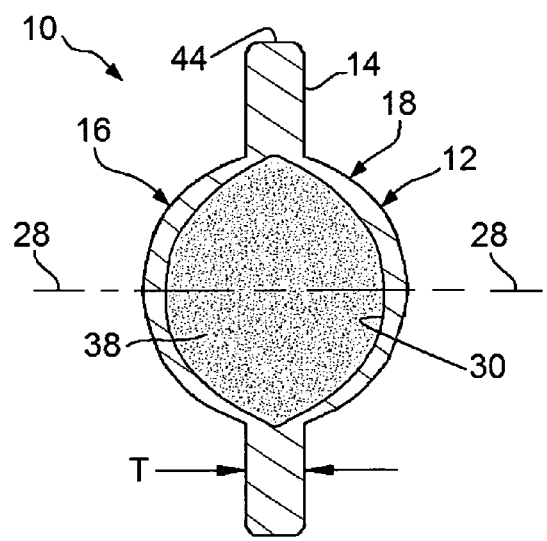
FIG. 7 shows a cross-section view of a third embodiment of lenses of the invention.

As illustrated in FIG. 3, a cross-section of the arcuate inner surface of anterior body member 16 generally resembles a circular configuration. However, as is well illustrated in FIGS. 6 and 7, an arcuate inner surface of either or both of anterior body member 16 or posterior body member 18 can deviate substantially from a true circular, e.g. hemispherical path. Both FIGS. 6 and 7 illustrate compound arcuate paths where the radii of curvature change along the progression of the arcuate path of the respective inner surface 20 or 24. However, in typical embodiments, a cross-section of the lens body reveals symmetry of the arcuate inner surface with respect to the vision axis.

Referring to FIG. 3, the configuration of the arcuate path of inner surface 20 is the same as the configuration of the arcuate path of outer surface 22, off-set in that the origins of the arc segments in inner surface 20 are displaced along vision axis 28 from the origins of the arc segments in outer surface 22. Accordingly, and as illustrated in FIG. 3, the thickness of the anterior body member is represented by relatively greater dimensions at locations proximate the vision axis and is represented by relatively lesser dimensions at portions 37 of the anterior body member which are remote from the vision axis.

The thickness of the posterior body member is generally constant, and is generally greater than the thickness of the anterior body member, about the majority of the projected area of the posterior body member, namely all of the posterior body member except that portion 36 of the posterior body member which is remote from the vision axis.

The lens body can be made from material which comprises, for example and without limitation, a silicone composition such as is known for use in intraocular lenses. Such silicone composition is resiliently elastic and compressible, but retains good restorative dimensional memory. Other shell membrane materials can be used such as, for example and without limitation, polymerized collagen (Collamer, manufactured by Staar Surgical, Inc.), Monrovia, Calif., elastic acrylic polymers, combinations of collamer and hydroxyethyl methacrylate, and other clear, e.g. transparent, flexible bio-compatible materials well known in the art as being suitable for use in optical applications.

Cavity 30 is filled with optical liquid 38. Liquid 38 is a viscous liquid which, in one embodiment of the invention can be silicone oil which has a refractive index of 1.4034, e.g. about 1.40, which material is known for use to fill the vitreous cavity in certain cases of retinal detachment and so is known to be bio-compatible. Optical liquid 38 does not contact the natural bio-intraocular structures of the eye, as the oil is enclosed entirely within the closed and sealed cavity 30 of the flexible lens body.

Other bio-compatible viscous materials, which can be used as the optical liquid, include chondroitin sulfate, hyaluronic acid and its hyaluronate salts, optionally mixed with e.g. saline solution, to obtain fairly precise desired refractive indices such as at or above 1.4. A variety of other viscous gels having suitable refractive index, can be used. Any such gel must be visually transparent, must have a refractive index greater than the refractive index of water, e.g. above about 1.33, and must be bio-compatible with respect to the use environment. Given these rather broad parameters, a substantial range of material compositions are acceptable as the contained interior substance.

The viscosity of optical liquid 38 is substantially greater than the viscosity of water, but liquid 38 must be sufficiently pliable to easily conform to any changes in curvature of the adjacent body member which may be urged on the lens body.

In general, optical liquid 38 reflects the character of a gel, while being readily deformable when so urged by the anterior body member and/or the posterior body member.

Accordingly, liquid 38 typically has a viscosity of about 4000 millipoise to about 7,000,000 millipoise, optionally about 30,000 to about 3,000,000 millipoise. One known acceptable gel has a stated viscosity of 30,000 to 50,000 centistokes (cSt). The viscosity can, of course, be adjusted by incorporation, in the optical liquid, of viscosity change agents known to those skilled in the gel arts.

Optical liquid 38 can also have the quality of circular or orthogonal birefringence. Birefringence is the quality of materials wherein light of certain polarities, either orthogonal as in traditional polarizing lenses, or circular polarity, has two refractive indices. Such birefringence can be obtained by mixing two materials having the different, e.g. refringent indices. Example of such mixture is a mixture of dextrorotary and levo-rotary biologic sugars and/or amino acids. So long as the two refractive indices differ by a significant amount, the lens is birefringent, and thus bifocal. Such lens focuses light of one polarity at a relatively greater distance, and light of a different polarity at lesser distances. Such birefringence increases the bifocal effect of the lens, but is not essential for lens function in this invention.

Lens body 12 can be fabricated with cavity 30 being empty. A sealable valve is assembled to the lens body, out of the line of sight of the eye, thus away from vision axis 28. The gel is filled into cavity 30 through the resealable valve.

The function of the lens, as an accommodating lens in this invention, depends primarily on the change in the arcuate shape of the lens body, which change occurs as an act of accommodation. The change in shape is provided by the combination of flexing of the shell material e.g. anterior body member 16, and fluidity of optical liquid 38 in response to an action of the ciliary muscle.

FIG. 5 illustrates the lens of FIGS. 1-4 installed in a human eye 40, it being understood that lenses of the invention can also be installed in the eyes of various animal species. As illustrated in FIG. 5, the natural lens has been removed, such as in a cataract surgery.

The natural capsular bag 42, which previously enclosed the natural lens is largely in place, though part of the anterior portion of the natural bag has been removed in the embodiment illustrated in FIG. 5.

Lens 10 is positioned such that distal edges 44 of flanges 14 are disposed against the inner surface 46 of the outer perimeter 48 of the capsule bag. The capsule bag remains attached to the ciliary muscle 50 through zonules 52. However, flanges 14, in the embodiment illustrated, are of sufficient length that the flanges expand the outer perimeter of the capsule bag such that the outer perimeter of the bag is proximate the ciliary muscle. Accordingly, even modest contraction of the ciliary muscle is effective to push against the distal edges of flanges 14.

Lens 10 generally works as follows. When the eye tries to focus on a near object, the ciliary muscle 50, illustrated in FIGS. 5 and 8, contracts inward, pushing inward on the lens zonules, and on the outer perimeter 48 of the capsule bag, while also raising pressure in the vitreous gel behind the lens. The centripetal force of the contracting ciliary muscle is transmitted inwardly, through the capsule bag to the distal edges of flanges 14, and through flanges 14 toward the vision axis, thus to reduce the e.g. diameter of outer perimeter 27 of the lens body. As the size of the outer perimeter of the lens body decreases, the maximum diameter of the anterior body member correspondingly decreases. The anterior body member is fabricated, in the embodiment illustrated in FIGS. 1-5, to be more readily flexed than the posterior body member. Accordingly, a disproportionate share of the flexing, which is imposed by the ciliary muscle on flanges 14, is absorbed by the anterior body member. The physical response of the anterior body member is expressed as an inward flexing of the remote portions 37 of the anterior body member, e.g. adjacent the outer perimeter of the lens body.

The inward flexing of the anterior body member at the outer perimeter is accompanied by generally reduced radius of curvature of anterior body member 16 as the anterior body member flexes to accommodate the reduction in diameter of the lens body at outer perimeter 27. Such reduction in radius of curvature of the anterior body member urges a corresponding change in the curvature of the surface of optical liquid 38 which is disposed at the inner surface of the anterior body member. Such resulting change in the configuration of optical liquid 38 generates a change in the focal length of the lens. Such change in optical radius of curvature of the working optics, in this case optical liquid 38, changes the focal point of the lens in a multiplicative fashion, via Snell's law, wherein Power=(Difference in Indices)/(Radius of Curvature).

Lens assemblies which rely on linear e.g. translational, movement of a first lens body with respect to a second lens body, or simply movement of a lens body along the vision axis, to provide for change in focal length, rely on a linear relationship between the distance of movement of the lens body and the change in focal length.

By contrast, substantially greater multiplicative changes in focal length can be achieved by using the ciliary muscle to change primarily curvature of the lens rather than to cause primarily translation movement of the lens surfaces as in the conventional art. Thus, where change in focal length according to translational movement of the lens surfaces by action of the ciliary muscle is limited to about 1.5 diopters for a 1 mm translation of a lens, change in curvature of lenses of the invention, responsive to the same action of the ciliary muscle, can provide up to about 3.5 diopters change, optionally up to about 3 diopters change, further optionally up to about 2.5 diopters change, depending on the starting arcuate profile of the lens. The lens can, of course, be designed to deliver lesser degrees of change, such as up to about 2.0 diopters, or less, as desired.

FIG. 6 illustrates a second embodiment of accommodating intraocular lenses of the invention. In the lens of FIG. 6, anterior body member 16 is convex as in the embodiment of FIGS. 1-5, thus to provide basis for efficient change in focal length with change in activity of the ciliary muscle. Posterior body member 18 is, contrary to the embodiment of FIGS. 1-5, mildly concave, or planar, or recessed planar as shown, so as to accommodate e.g. a bulging profile on the vitreous humor, or where the depth of the lens cavity, between the vitreous cavity and the natural iris 54 is insufficient to properly receive a lens which is configured as in FIGS. 1-5 where the posterior body member is planar, and not recessed. As in the embodiments of FIGS. 1-5, both anterior body member 16 and posterior body member 18 are shown to be symmetrical with respect to the vision axis.

Figure 8:
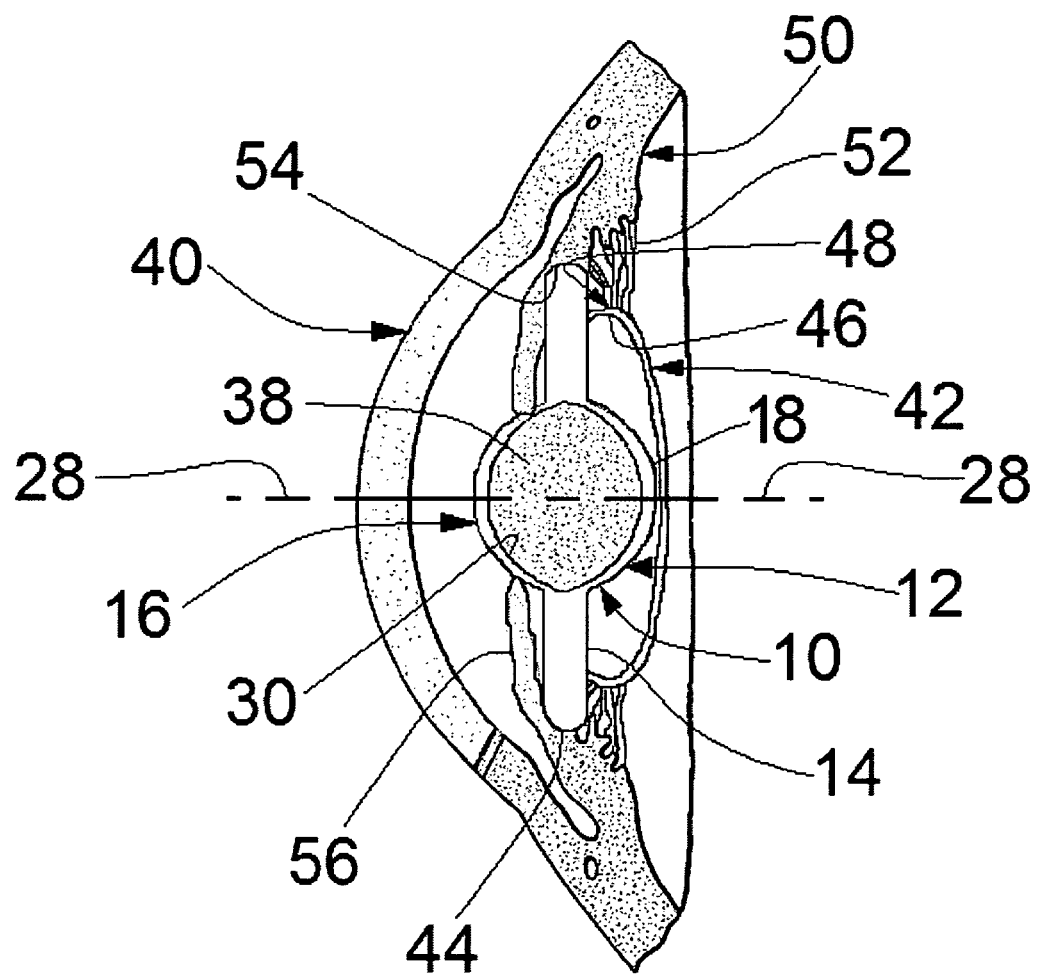
FIG. 8 is a cross-section view illustrating the embodiment of FIG. 7, implanted in an eye.

FIGS. 7 and 8 show another modified version of the lenses of FIGS. 1-6. The lens of FIGS. 7 and 8 have flanges 14 which are designed to fit directly into the ciliary sulcus 54, e.g. directly against the ciliary muscle. In the assembly shown in FIG. 8, flanges 14 are outside, e.g. in front of, the capsular bag, and in direct contact with the contracting ciliary muscle 50. Contraction of muscle 50 applies force directly onto flanges 14. Flanges 14 transmit the forces to lens body 12, thus directly compressing the lens body at outer perimeter 27 of the lens body.

Such compressing of the lens body at outer perimeter 27 shortens the radii of curvature of both the anterior body member and the posterior body member, and achieves a high degree of accommodation, potentially higher than any accommodation which would accompany a corresponding muscle contraction in connection with a lens of FIGS. 1-5, or FIG. 6.

Such increase in degree of accommodation results from the fact that both of body members 16 and 18 are convex. Namely, the convex nature of liquid 38 is established at the inner surface of the anterior body member as well as at the inner surface of the posterior body member. With convex curvature at both the anterior surface of liquid 38 and at the posterior surface of liquid 38, light rays incident on the lens are treated to both a first anterior focal length adjustment, and to a second posterior focal length adjustment.

In general, placing flanges 14 in the sulcus is less preferred than placing the flanges in the capsule bag. However, in some instances, the lenses of FIGS. 1-6, wherein only the anterior body member is convex, are deficient in terms of the diopter adjustment which can be achieved.

Where greater diopter power is required, the double-convex lens of FIG. 7 is available to provide such optical power. However, where the double-convex lens of FIG. 7 is selected, it is quite possible that the front-to-back distance, between the vitreous chamber and generally up to the iris of the eye, may be too small to receive the front-to-back dimension of the lens of FIG. 7. In such instance, flanges 14 are positioned relatively frontwardly in the lens cavity, and are positioned in the sulcus, in order that the back of the lens body be in front of, e.g. displaced from, the vitreous chamber, as illustrated in FIG. 8. As illustrated in FIG. 8, in such instance, the front of the lens may extend frontwardly of the natural iris 56.

Still referring to the embodiments of FIGS. 7 and 8, compressing one or both of the body members 16, 18, at outer perimeter 27, shortens the radius of curvature of the anterior body member and the posterior body member, both generally about vision axis 28, whereby the shape of the lens is reconfigured more toward a spherical shape.

The forces of ciliary contraction during accommodation may not transmit directly through zonules 52 to the capsular bag. The zonules are a loose network of fibers, and so the zonules might slacken when the ciliary body contracts. The exact mechanism of operation of zonules is still not fully settled among ophthalmologists and physiologists.

Figure 9:
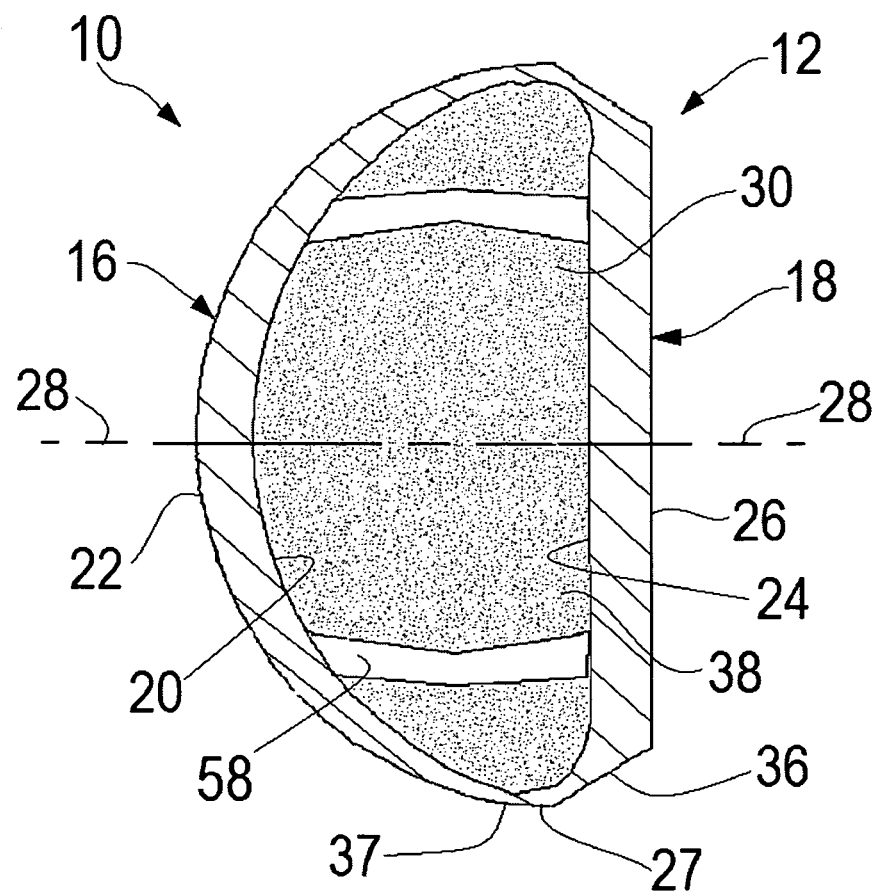
FIG. 9 shows a cross-section view of a fourth embodiment of lenses of the invention.

FIG. 9 shows, as a further embodiment, a relatively larger lens, which fits snugly within the capsular bag. This lens has anterior 16 and posterior 18 body members enclosing viscous optical liquid 38, but is devoid of flanges 14. Inside the lens body are first and second struts 58. Struts 58 can optionally extend 360 degrees around vision axis 28, either intermittently, or as a single continuous strut body, on the interior of the shell. Struts 58 are resiliently compressed front-to-rear when the ciliary muscle is relaxed, and in the non-accommodating state. As the ciliary muscle contracts, the restorative forces in struts 58 push the anterior and posterior body members away from each other, front-to-rear, thus to accommodate near vision. The design of the strut allows the strut to bend only outward, away from vision axis 28. This action, of pushing the anterior and posterior body members away from each other, shortens the radius of curvature of e.g. the anterior body member in a fashion similar to natural shortening of the radius of curvature, accommodation, in a natural lens. In some embodiments, posterior body member 18 can have an outwardly convex arcuate configuration as illustrated in FIGS. 7 and 8. In some embodiments, both the anterior body member and the posterior body member have outwardly convex arcuate configurations.

Calculations of the needed curvatures of the anterior and posterior optical surfaces of the anterior 16 and posterior 18 body members, to enable focusing of light at distance when the eye is in a relaxed state can be realized using the matrix system of optical calculations which are described, for example, by Langenbucher et al in Ophthal. Phyisol. Opt. 2004 24:450-457, herein incorporated by reference in its entirety.

In all of the lens embodiments of FIGS. 1-9, the outer body members 16 and 18 are thinnest at or adjacent outer perimeter 27 of lens body 12, optionally proximate flange 14 in the embodiments of FIGS. 1-8. Forces from the ciliary muscle are transferred through flanges 14 to body members 16, 18. Given the relatively thinner portions of the body members proximate flanges 14, the body members flex to a greater extent proximate flanges 14 than farther away from the flanges, and thereby shorten the radius of curvature of the optical surfaces of body members 16, 18, thereby to effect diopter change in the lens body primarily through corresponding curvature changes in the contained optical liquid 38.

In the embodiments of FIGS. 1-5, posterior body member 18 is substantially flat, planar, and thus lacks any optical power. The posterior body member is also thicker than the anterior body member in such embodiments, whereby the degree of change in curvature of the anterior body member, expressed as distance of translation of the anterior body member perpendicular to the profile of the anterior body member, is substantially greater than the degree of change, if any, in the curvature in the posterior body member. The embodiments of FIGS. 3 and 6 may enable transmission of the pressure rise in the posterior vitreous chamber to assist in changing the anterior radius of curvature, thereby increasing near focusing, namely accommodating, power.

The function of lens 10 as an accommodating lens depends primarily on the change in shape of the lens as the act of accommodation. When the e.g. human eye tries to focus on a near object, the ciliary muscle contracts inward, pushing inward on the lens zonules, and also raising pressure in the vitreous chamber which is behind the lens. The centripetal force of the contracting ciliary muscle is transmitted through the lens flange 14, compressing the lens body at outer perimeter 27. Compressing the lens body at outer perimeter 27 shortens the radius of curvature of the anterior body member in the embodiments of FIGS. 1-6, and shortens the radius of curvature of both the anterior and posterior body members in the embodiment of FIGS. 7 and 8. In all of the lens embodiments of FIGS. 1 through 8, the lens body is relatively thinner at the juncture of the anterior and posterior shells with flange 14, e.g. at outer perimeter 27. In this scenario, the forces received from flanges 14 are absorbed largely in shortening the radius of curvature of the optical surfaces, rather than largely being absorbed in translation of the anterior body member further away from the posterior body member.

This is in contrast to translation of the body members where the power changes depend on position in the eye and axial length of the eye. For this reason, the lenses of the invention offer greater diopter ranges than lenses which operate according to translation of one or more of the lens elements.

As indicated above, with the exception of the embodiments of FIG. 9, the force of the ciliary muscle is received at distal edges 44 of flanges 14. The muscle force is transmitted through flanges 14 toward lens body 12, and is received at lens body 12 at or adjacent outer perimeter 27. Such force acts, through outer perimeter 27, on the lens body to re-shape the curvature of the anterior and/or posterior body members, thus to effect change in focal length of the lens body.

Thus it is critical that the flanges, where used, have sufficient rigidity that the contraction forces of the ciliary muscle are transmitted to the lens body in sufficient intensity to effect accommodation of the lens body in accord with the accommodative vision needs being expressed by the ciliary muscle.

To that end, flanges 14 can be specified in terms of thickness "T" sufficient to provide the required level of rigidity which is effective to transmit the ciliary muscle forces. The particular dimension of thickness "T" depends on the rigidity of the material composition selected for flange 14, and can be well selected by those skilled in the art.

In the alternative, the composition of the material used to make flanges 14 can be different from the material used to make lens body 12. Thus, the material used to make flanges 14 can be more rigid than the material used in making body members 16, 18, thus to achieve rigidity by material selection.

As used herein "optical liquid" includes gels, which might not otherwise be considered liquids, to the extent the shape of the gel mass can be readily changed by action of the ciliary muscle. Thus, "optical liquid" does include gel compositions which have viscosity similar to the viscosity of the lens matrix in a youthful natural eye.

The following matrix calculations are performed using the model eye and its parameters as developed by Gullstrand. The measurements are taken from the average distances and radii of curvature of the Gullstrand Model Eye.

| Radius of Curvature (meters) of Eye Surfaces | | Indices of Refraction | | Translation Distances (Meters) | |
|---|---|---|---|---|---|
| 0.0078 | Cornea Exterior | 1.000 | Air | Cornea | 0.00055 |
| 0.0065 | Cornea Interior | 1.3771 | Cornea | Ant. Chamber | 0.003 |
| 0.009 | IOL Anterior | 1.3374 | Aqueous | Lens Thickness | 0.003 |
| 0100 | IOL Posterior | 1.4034 | Silicone Oil | Vitreous | 0.01821 |
| 0 | | 1.336 | Vitreous | | 0 |
| $R :=$ 00 | | $N :=$ 0 | | $t :=$ 0 | |
| 0 | | 0 | | 0 | |
| 0 | | 0 | | 0 | |
| 0 | | 0 | | 0 | |
| 0 | | 0 | | 0 | |

The above "R", "N", and "t" vectors are referenced by their respective indices as follows $$Pc1 := \frac{N_1 - N_0}{R_0} \quad Dc := \frac{t_0}{N_1} \quad Vit := t_3$$

$$Pc2 := \frac{N_2 - N_1}{R_1} \quad Da := \frac{t_1}{N_2}$$

$$Pi2 := \frac{N_4 - N_3}{R_3} \quad Di := \frac{t_2}{N_3}$$

Any lens system, including the eye, can be calculated using a series of multiplied matrices, with the first refracting surface, in the case of the invention the exterior of the cornea on the far right, followed by a translation matrix with reduced distance Dc, then the next surface, namely the posterior cornea, right to left $$Sys := \begin{pmatrix} 1 & Pi2 \\ 0 & 1 \end{pmatrix} \cdot$$

-continued
$$\begin{pmatrix} 1 & 0 \\ Di & 1 \end{pmatrix} \cdot \left[ \begin{pmatrix} 1 & -Pil \\ 0 & 1 \end{pmatrix} \cdot \begin{pmatrix} 1 & 0 \\ Da & 1 \end{pmatrix} \cdot \begin{pmatrix} 1 & -Pc2 \\ 0 & 1 \end{pmatrix} \cdot \begin{pmatrix} 1 & 0 \\ Dc & 1 \end{pmatrix} \cdot \begin{pmatrix} 1 & -Pc1 \\ 0 & 1 \end{pmatrix} \right]$$

The Basic System

Expanding this matrix into a single product matrix can provide the equation illustrated as FIG. 10.

Solving that equation for Pi1:=1, and given the second focal point as Vit (t3), provides the equation illustrated in FIG. 11

Find (Pi1)=18.34277 This is the refracting power of the anterior surface of the intraocular lens.

$$Ri1 := \frac{N_3 - N_2}{18.343}$$

By Snell's Law

Ri1=0.0036 Radius of anterior lens surface at rest (in meters)

If the optic is 0.006 m in diameter, then the angle of arc is: $\alpha := 0$ rad Given $$\sin(\alpha) = \left(\frac{0.003}{Ri1}\right)$$

Find ($\alpha$)=0.98591 Radians $$\frac{0.003}{0.0036} = 0.83333 \text{ rad}$$

$$0.986 \frac{180}{2 \cdot \pi} = 28.24682$$

degrees in the relaxed state

The half length on the arc 12:=Ri1·0.986

12=0.00355(meters,■) or 12×1000·=3.54773 mm

Suppose the lens pinches with accommodation 0.0005 meters, or 0.5 mm total—since the arc length has to be constant, the new angle of the half arc is $$\theta := 0$$

Given that $$\frac{12 \cdot \sin(\theta)}{\theta} = 0.00275$$

$$\text{Find}(\theta) = 1.2045$$

The new radius is $$R6 := \frac{0.00275}{\sin(1.2045 \cdot \text{rad})}$$

$$R6 = 0.00295$$

$$Power_2 := \frac{N_3 - N_2}{R6}$$

Power$_2$=22.40785 This is the power attainable in accommodation

Power$_2$−18.3472=4.06065 This small change in curvature yields 4 diopters of accommodation Those skilled in the art will now see that certain modifications can be made to the apparatus and methods herein disclosed with respect to the illustrated embodiments, without departing from the spirit of the instant invention. And while the invention has been described above with respect to the preferred embodiments, it will be understood that the invention is adapted to numerous rearrangements, modifications, and alterations, and all such arrangements, modifications, and alterations are intended to be within the scope of the appended claims.

To the extent the following claims use means plus function language, it is not meant to include there, or in the instant specification, anything not structurally equivalent to what is shown in the embodiments disclosed in the specification.

Having thus described the invention, what is claimed is:

1. An accommodating intraocular lens, comprising:
   (a) an optical lens body having an anterior body member and a posterior body member, joined to each other, said optical lens body defining a vision axis;
   (b) a cavity being defined, and enclosed between, said anterior body member and said posterior body member;
   (c) one or more compressible struts in the cavity, extending between said anterior body member and said posterior body member, said one or more struts being displaced from the vision axis and having first and second ends, said one or more struts being configured to flex away from the vision axis when the first and second ends of said one or more struts are compressed toward each other; and
   (d) a bio-compatible liquid filling in the cavity, the liquid having a refractive index greater than the refractive index of water.

2. An accommodating intraocular lens as in claim 1 wherein said anterior body member has a convex outer surface and wherein said posterior body member has a planar, or recessed inner surface.

3. An accommodating intraocular lens as in claim 2 wherein said posterior body member is more rigid than said anterior body member, whereby imposition of an inwardly-directed force against an outer perimeter of said lens body results in deflection of said anterior body member in preference to deflection of said posterior body member.

4. An accommodating intraocular lens as in claim 1, said anterior body member having inner and outer surfaces, the outer surface of said anterior body member defining a convex configuration.

5. An accommodating intraocular lens as in claim 4, each of the inner and outer surfaces of the anterior body member being defined by a single center of rotation.

6. An accommodating intraocular lens as in claim 4, at least one of the inner and outer surfaces of the anterior body member being defined by multiple centers of rotation.

7. An accommodating intraocular lens as in claim 1 wherein the composition of said anterior body member and said posterior body member are selected from the group consisting of optical grade silicone, polymerized collagen, optical elastic acrylic polymer, collamer, and combinations of collamer and hydroxyethyl methacrylate.

8. An accommodating intraocular lens as in claim 1 wherein the composition of said bio-compatible filling liquid is selected from the group consisting of silicone oil, hyaluronic acid, and salts of hyaluronic acid.

9. An accommodating intraocular lens as in claim 1 wherein said bio-compatible filling liquid has a refractive index of at least 1.35.

10. An accommodating intraocular lens as in claim 1 wherein said bio-compatible filling liquid has a refractive index of at least 1.40.

11. An accommodating intraocular lens as in claim 1 wherein said bio-compatible filling liquid comprises material which is birefringent, having at least first and second refractive indices, sufficiently different from each other to provide a distinct bifocal functionality to said intraocular lens.

12. An accommodating intraocular lens as in claim 1, said anterior body member having a generally arcuate three-dimensional outer surface.

13. An accommodating intraocular lens as in claim 1, said posterior body member having a generally arcuate three dimensional outer surface.

14. An accommodating intraocular lens as in claim 1, wherein a scope of vision is associated with the vision axis, said one or more struts being outside the scope of vision.

15. An accommodating intraocular lens as in claim 1, said one or more compressible struts extending 360 degrees about the vision axis.

16. An accommodating intraocular lens as in claim 15, said one or more struts comprising intermittent expression of such one or more struts about the vision axis.

17. An accommodating intraocular lens as in claim 1 wherein, when said lens is resident as a lens implant in an eye having a ciliary muscle, with the ciliary muscle against said lens, as the ciliary muscle contracts, restorative forces in said one or more struts push the anterior body member and the posterior body member away from each other.

18. An accommodating intraocular lens as in claim 1, said one or more struts comprising intermittent expression of such one or more struts about the vision axis.

* * * * *